United States Patent [19]

Petitpierre

[11] 4,281,855
[45] Aug. 4, 1981

[54] PRESSURE-SENSITIVE OR HEAT-SENSITIVE RECORDING MATERIAL AND NOVEL 2,2-DIARYLCHROMENO COMPOUNDS USED THEREIN

[75] Inventor: Jean C. Petitpierre, Kaiseraugst, Switzerland

[73] Assignee: Ciba-Geigy Corporation, Ardsley, N.Y.

[21] Appl. No.: 51,556

[22] Filed: Jun. 25, 1979

Related U.S. Application Data

[62] Division of Ser. No. 873,582, Jan. 30, 1978, Pat. No. 4,187,233.

[30] Foreign Application Priority Data

Feb. 4, 1977 [CH] Switzerland .................... 1379/77

[51] Int. Cl.³ .................... B41M 5/16; B41M 5/18; B41M 5/22
[52] U.S. Cl. .................... 282/27.5; 427/151; 428/307; 428/537; 428/913; 428/914
[58] Field of Search .................... 282/27.5; 427/151; 428/307, 411, 537, 913, 914; 260/345.2

[56] References Cited

U.S. PATENT DOCUMENTS

| | | | |
|---|---|---|---|
| 3,904,642 | 9/1975 | Mach et al. | 260/345.2 |
| 3,910,912 | 10/1975 | Scheuermann et al. | 260/345.2 |
| 4,094,877 | 6/1978 | Crounse et al. | 428/307 |
| 4,147,509 | 4/1979 | Baumann et al. | 282/27.5 |

*Primary Examiner*—Bruce H. Hess
*Attorney, Agent, or Firm*—Edward McC. Roberts; John P. Spitals

[57] ABSTRACT

A pressure- or heat-sensitive recording material which contains as color former at least one 2,2-diarylchromeno compound of the formula

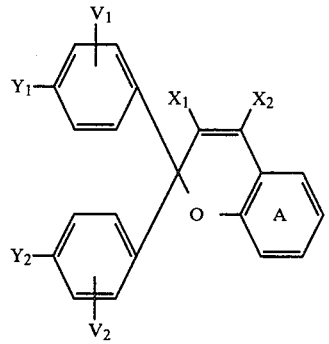

wherein
$V_1$ and $V_2$, each independently of the other, represent hydrogen, halogen, lower alkyl or lower alkoxy,
$Y_1$ and $Y_2$, each independently of the other, represent hydrogen, —O—$R_1$ or

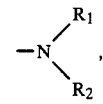

$X_1$ and $X_2$, each independently of the other, represent hydrogen, alkyl of up to 12 carbon atoms which is unsubstituted or substituted by halogen, or represent benzyl, phenyl, or benzyl or phenyl which is substituted by halogen, nitro, lower alkyl, lower alkoxy or the amino group

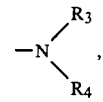

and
the ring A is unsubstituted or substituted by halogen, nitro, lower alkyl, —O—$R_5$ or

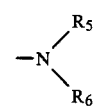

or contains a fused benzene ring, and
$R_1$, $R_2$, $R_3$, $R_4$, $R_5$ and $R_6$, each independently of the other, represent alkyl of not more than 12 carbon atoms which is unsubstituted or substituted by halogen hydroxyl, cyano or lower alkoxy, or represents cycloalkyl, phenyl, benzyl, or phenyl or benzyl which is substituted by halogen, nitro, lower alkyl or lower alkoxy, or each of the pair of substituents $R_1$ and $R_2$, $R_3$ and $R_4$, $R_5$ and $R_6$, together with the nitrogen atom to which said pair is attached, forms a 5- or 6-membered heterocyclic radical.

19 Claims, No Drawings

PRESSURE-SENSITIVE OR HEAT-SENSITIVE RECORDING MATERIAL AND NOVEL 2,2-DIARYLCHROMENO COMPOUNDS USED THEREIN

This is a Divisional of application Ser. No. 873,582 filed on Jan. 30, 1978, now U.S. Pat. No. 4,187,233.

The present invention relates to pressure- or heat-sensitive recording material which contains as colour former in its colour forming system at least one 2,2-diarylchromeno compound of the general formula

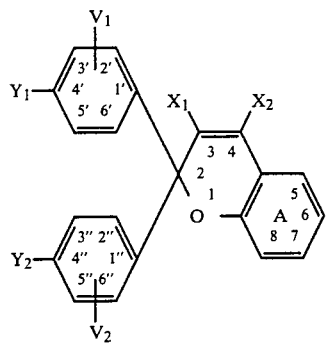

wherein $V_1$ and $V_2$, each independently of the other, represent hydrogen, halogen, lower alkyl or lower alkoxy, $Y_1$ and $Y_2$, each independently of the other, represent hydrogen, —O—$R_1$ or

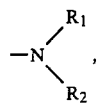

$X_1$ and $X_2$, each independently of the other, represent hydrogen, alkyl of up to 12 carbon atoms which is unsubstituted or substituted by halogen, or represent benzyl, phenyl, or benzyl or phenyl which is substituted by halogen, nitro, lower alkyl, lower alkoxy or the amino group

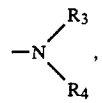

and
the ring A can be substituted by halogen, nitro, lower alkyl, —O—$R_5$ or

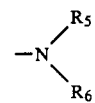

or can contain a fused benzene ring, and
$R_1$, $R_2$, $R_3$, $R_4$, $R_5$ and $R_6$, each independently of the other, represent alkyl of not more than 12 carbon atoms which is unsubstituted or substituted by halogen, hydroxyl, cyano or lower alkoxy, or represents cycloalkyl, phenyl, benzyl, or phenyl or benzyl which is substituted by halogen, nitro, lower alkyl or lower alkoxy, or each of the pair of substituents $R_1$ and $R_2$, $R_3$ and $R_4$, $R_5$ and $R_6$, together with the nitrogen atom to which said pair is attached, forms a 5- or 6-membered, preferably saturated, heterocyclic radical.

Preferably at least one of the radicals $Y_1$ und $Y_2$ or of the substituents of the ring A is a group of the formula

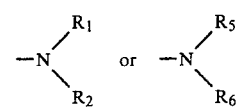

In the definition of the radicals of the chromeno compounds, lower alkyl and lower alkoxy generally denote those groups or group components which contain 1 to 5, especially 1 to 3, carbon atoms, for example methyl, ethyl, n-propyl, isopropyl, n-butyl, sec-butyl or amyl, and methoxy, ethoxy or isopropoxy. Halogen in connection with all substituents referred to in this specification represents for example fluorine, bromine, or preferably chlorine.

The radicals $Y_1$ and $Y_2$ can be different or they are preferably identical. $V_1$ and $V_2$ are also preferably identical radicals.

Alkyl radicals represented by $X_1$, $X_2$ and $R_1$ to $R_6$ can be straight-chain or branched. Examples of such alkyl radicals are: methyl, ethyl, n-propyl, isopropyl, n-butyl, sec-butyl, n-hexyl, n-octyl or n-dodecyl.

Substituted alkyl radicals $X_1$, $X_2$ and $R_1$ to $R_6$ are in particular halogenalkyl, cyanoalkyl, hydroxyalkyl, alkoxyalkyl, each containing 2 to 4 carbon atoms, for example $\beta$-chloroethyl, $\beta$-cyanoethyl, $\beta$-hydroxyethyl, $\beta$-methoxyethyl or $\beta$-ethoxyethyl.

Cycloalkyl represented by $R_1$ to $R_6$ is cyclopentyl or preferably cyclohexyl.

Preferred substituents in the benzyl or phenyl moiety of the radicals X and R are for example halogen, nitro, methyl or methoxy. Examples of such araliphatic and aromatic radicals are: p-methylbenzyl, o- or p-chlorobenzyl, o- or p-nitrobenzyl, o- or p-tolyl, xylyl, o-, m- or p-chlorphenyl or o- or p-methoxyphenyl, o- or p-nitrophenyl.

The phenyl moiety of the radicals X, especially of $X_2$, can advantageously contain an amino group

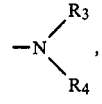

in which $R_3$ and $R_4$ represent in particular lower alkyl, for example methyl or ethyl, or benzyl. Examples of amino-substituted phenyl radicals X are in particular p-dimethylaminophenyl, p-diethylaminophenyl and p-dibenzylaminophenyl.

A heterocyclic radical represented by each of the pair of substituents $R_1$ and $R_2$, $R_3$ and $R_4$ and $R_5$ and $R_6$, together with the nitrogen atom to which said pair is attached, is for example pyrrolidino, piperidino, pipecolino, morpholino, thiomorpholino or piperazino.

The substituents $X_1$ and $X_2$, each independently of the other, preferably represent hydrogen, lower alkyl, benzyl or phenyl, whilst the radicals $R_1$ to $R_6$ preferably represent lower alkyl, benzyl or phenyl. $V_1$ and $V_2$ preferably represent hydrogen, methyl, methoxy, ethoxy or chlorine.

The ring A is not further substituted or it can contain as substituents preferably halogen, nitro, lower alkyl, lower alkoxy or a fused benzene ring. Most preferably, the ring A contains in the 7-position an amino group which is preferably mono- or disubstituted by lower alkyl, especially by methyl or ethyl.

Chromeno compounds having an important utility are those of the formula

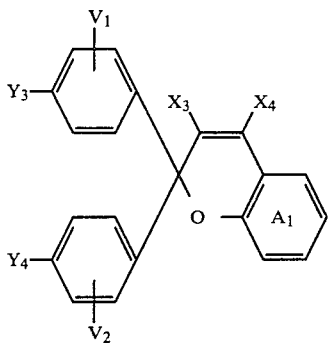

(2)

wherein $V_1$ and $V_2$ have the given meanings, $Y_3$ and $Y_4$, each independently of the other, represent hydrogen, —O—$R_7$ or

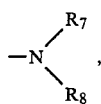

$X_3$ represents hydrogen, lower alkyl, benzyl, phenyl, or benzyl which is substituted by halogen, $X_4$ represents hydrogen, lower alkyl, benzyl, phenyl, benzyl which is substituted by halogen or lower alkyl, or phenyl which is substituted by halogen, nitro, lower alkyl, lower alkoxy or by the amino group

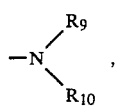

and
the ring $A_1$ can be substituted by halogen, nitro, lower alkyl, —O—$R_{11}$ or

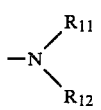

or can contain a fused benzene ring, whilst
$R_7$, $R_8$, $R_9$, $R_{10}$, $R_{11}$ and $R_{12}$, each independently of the other, represent alkyl of 1 to 12 carbon atoms, cycloalkyl, phenyl, benzyl, or phenyl or benzyl which is substituted by halogen, lower alkyl or lower alkoxy, or each of the pair of substituents $R_7$ and $R_8$, $R_9$ and $R_{10}$, $R_{11}$ and $R_{12}$, together with the nitrogen atom to which said pair is attached, represents a 5- or 6-membered heterocyclic ring.

Particularly interesting chromeno compounds are those of the general formula

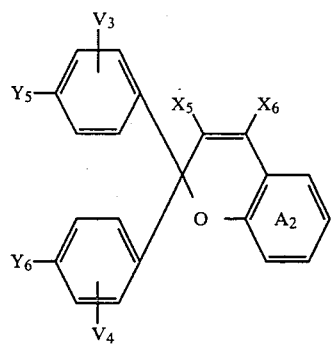

(3)

wherein $V_3$ and $V_4$, each independently of the other, represent hydrogen, chlorine, methyl, methoxy or ethoxy, $Y_5$ and $Y_6$, each independently of the other, represent hydrogen, lower alkoxy, phenoxy, benzyloxy or

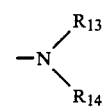

$X_5$ represents hydrogen or lower alkyl, and $X_6$ represents hydrogen, lower alkyl, benzyl or phenyl, and the ring $A_2$ can be substituted by halogen, nitro, or

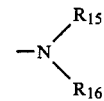

or can contain a fused benzene ring, whilst $R_{13}$, $R_{14}$, $R_{15}$ and $R_{16}$, each independently of the other, represent lower alkyl, phenyl or benzyl. Preferably the ring $A_2$ contains a di-lower alkylamino group.

Particularly preferred chromeno compounds of the formulae (1), (2) and (3) are those in which both radicals Y represent an amino group

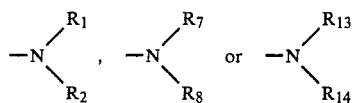

The chromeno compounds of the formulae (1) to (3) are partly known compounds, but constitute a novel class of colour formers. They can be obtained by methods which are known per se. For example, they can be obtained by reacting a compound of the formula

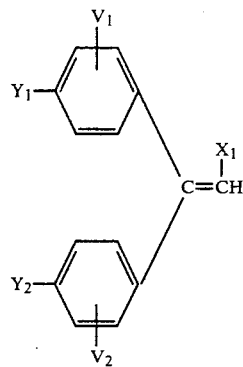

wherein $Y_1$, $Y_2$, $V_1$, $V_2$ and $X_1$ have the given meanings, with a keto compound of the formula

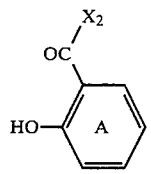

wherein A and $X_2$ have the given meanings.

The reaction is advantageously carried out in a polar solvent, preferably in a lower alkanol, for example ethanol, and at reflux temperature. Catalytic amounts of a lower aliphatic carboxylic acid, for example acetic acid, can be added to the reaction mixture.

A further embodiment of the process for obtaining the compounds of the formula (1), wherein $X_1$ represents hydrogen and the ring A is substituted in the 7-position by —O—$R_5$ or

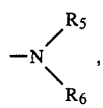

consists in reacting a compound of the formula

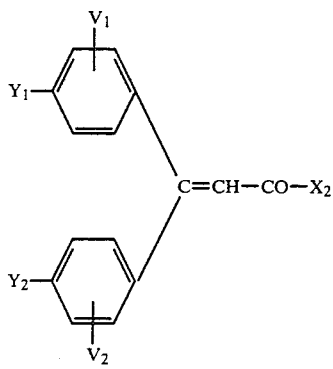

wherein $Y_1$, $Y_2$, $V_1$, $V_2$ and $X_2$ have the given meanings, with a phenol compound of the formula

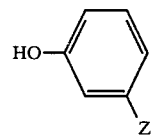

wherein Z represents —O—$R_5$ or

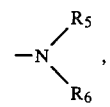

in which $R_5$ and $R_6$ have the given meanings.

A preferred process for the production of the compounds of the formula (1) comprises reacting by the Grignard method one mole of a coumarin compound of the formula

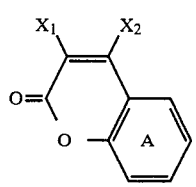

wherein $X_1$, $X_2$ and A have the given meanings, with 2 moles of a phenylmagnesium halide of the formula

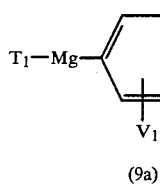  and/or  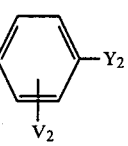

(9a)  (9b)

wherein each of $T_1$ and $T_2$ represents halogen, for example chlorine, bromine or iodine and A, $X_1$, $X_2$, $Y_1$, $Y_2$, $V_1$ and $V_2$ have the given meanings.

The present invention also relates to the novel compounds within the 2,2-diarylchromeno compounds of the formula (1) which have the formula

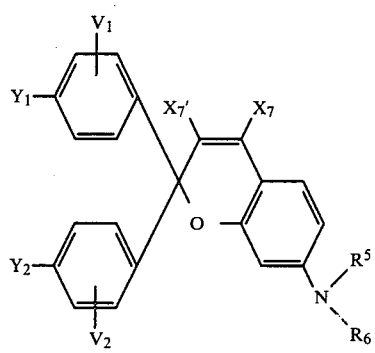

wherein $V_1$, $V_2$, $Y_1$, $Y_2$, $R_5$ and $R_6$ have the given meanings and each of $X_7$ and $X'_7$ represents hydrogen, alkyl of at most 12 carbon atoms which is unsubstituted or substituted by halogen, or represents benzyl or phenyl which is unsubstituted or substituted by halogen, nitro, lower alkyl, lower alkoxy or

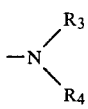

Preferred novel 2,2-diarylchromeno compounds have the formula

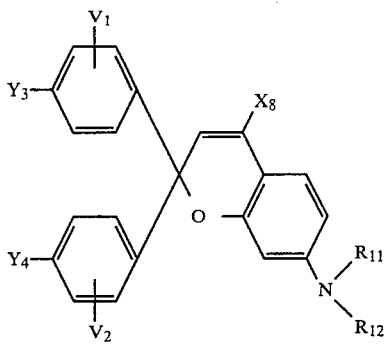

(10)

wherein $V_1$, $V_2$, $Y_3$, $Y_4$, $R_{11}$ and $R_{12}$ have the given meanings and $X_8$ represents hydrogen, lower alkyl, benzyl, phenyl, or benzyl which is substituted by halogen.

Particularly interesting novel 2,2-diarylchromeno compounds are those of the formula

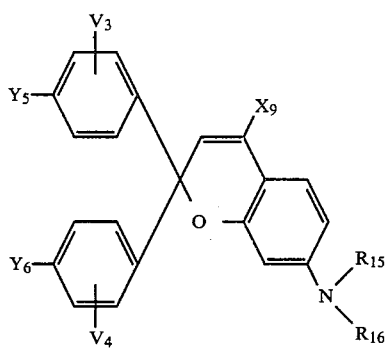

(11)

wherein $V_3$, $V_4$, $Y_5$, $Y_6$, $R_{15}$ and $R_{16}$ have the given meanings and $X_9$ represents hydrogen, lower alkyl, benzyl or phenyl.

Especially preferred novel 2,2-diarylchromeno compounds are those of the formula

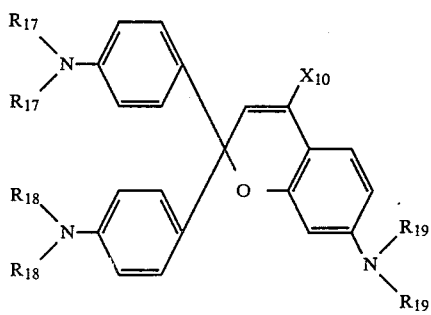

wherein each of $R_{17}$, $R_{18}$, $R_{19}$ and $X_{10}$ represents alkyl of 1 to 4 carbon atoms, preferably methyl or ethyl.

The definitions of the substituents $X_1$ and $X_2$ apply also by analogy to the radicals $X_7$ to $X_{10}$.

These novel 2,2-diarylchromeno compounds are to be singled out as especially advantageous colour formers.

The process for obtaining the novel 2,2-diarylchromeno compounds of the formula (9) comprises reacting by the Grignard method about 1 mole of a coumarin compound of the formula

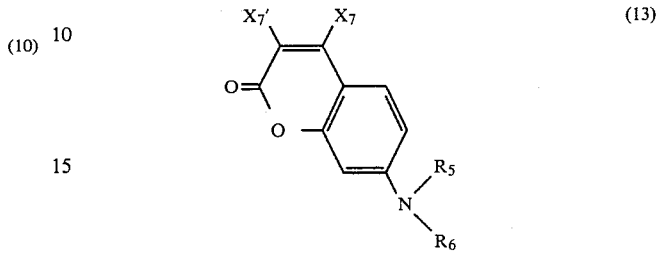

(13)

with about 2 moles of a phenylmagnesium halide of the formula (9a) and/or (9b).

The novel compounds of the formulae (10), (11) and (12) are obtained in analogous manner.

The chromeno compounds of the formulae (1) to (3) and (9) to (12) are normally colourless or faintly coloured. When these colour formers are brought into contact with a developer, i.e. an electron acceptor, they produce intense yellow to green colours of excellent light fastness. They are therefore also very useful when mixed with other known colour formers, for example 3,3-(bis-aminophenyl)-phthalides, 3,3-(bis-indolyl)-phthalides, 2,6-diaminofluoranes or spiropyranes, to produce blue, navy blue, grey or black colourations.

The chromeno compounds of the formula (1) exhibit an improved colour intensity and lightfastness both on clay and on phenolic substrates. They are chiefly suitable for use in a pressure-sensitive recording material, which can also be a copying material.

A pressure-sensitive material consists for example of at least one pair of sheets, which contain at least one colour former of the formula (1), dissolved in an organic solvent, and an electron acceptor as developer. The colour former effects a coloured marking at those points where it comes into contact with the electron acceptor.

Typical examples of such developers are attapulgite clay, silton clay, silica, bentonite, halloysite, aluminium oxide, aluminium sulphate, aluminium phosphate, zinc chloride, kaolin or any clay or organic compounds with acid reaction, for example unsubstituted or ring-substituted phenols, salicyclic acid or esters of salicyclic acid and the metal salts thereof, or an acid polymeric material, for example a phenolic polymer, an alkylphenolacetylene resin, a maleic acid/rosin resin or a partially or completely hydrolysed polymer of maleic acid and styrene, ethylene, vinyl methyl ether or carboxypolymethylene. Preferred developers are attapulgite clay, silton clay or phenolformaldehyde resin. These electron acceptors are preferably applied in the form of a layer to the face of the receiving sheet.

In order to prevent the colour formers contained in the pressure-sensitive recording material from becoming active too soon, they are usually separated from the electron acceptor, for example by incorporating the colour formers in foam-like, sponge-like or honeycomb-like structures. Preferably the colour formers are enclosed in microcapsules.

When the capsules are ruptured by pressure, for example with a pencil, and the colour former solution is thereby transferred to an adjacent sheet which is coated with an electron acceptor, a coloured area is produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example polyhalogenated diphenyl, such as trichlorophenyl or a mixture thereof with liquid paraffin; tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of diphenyl, naphthalene or triphenyl, terphenyls, partially hydrogenated terphenyl, or other chlorinated or hydrogenated condensed aromatic hydrocarbons.

The capsule walls can be formed evenly around the droplets of the colour former solution by coacervation, and the encapsulating material can consist of gelatin and gum arabic, as described e.g. in U.S. Pat. No. 2,800,457.

The capsules can be formed preferably also from an aminoplast or from modified aminoplasts by polycondensation, as described in the British Pat. Nos. 989,264; 1,156,725; 1,301,052 and 1,355,124.

The microcapsules containing the colour formers of formula (1) can be used for the production of a wide variety of known kinds of pressure-sensitive copying material. The various systems differ substantially from one another in the arrangement of the capsules, the colour reactants and the carrier material.

A preferred arrangement is that in which the encapsulated colour former is applied as a layer to the back of a transfer sheet and the electron acceptor substance as a layer to the face of a receiving sheet. However the components can also be used in the paper pulp.

Another arrangement of the constituents consists in the microcapsules which contain the colour former, and the developer, being in or on the same sheet in the form of one or more individual layers or being present in the paper pulp.

Such pressure-sensitive copying materials are described, for example, in U.S. Pat. Nos. 2,730,457, 2,932,582, 3,418,250, 3,418,656, 3,427,180 and 3,516,846. Further systems are described in British Pat. Nos. 1,042,596, 1,042,597, 1,042,598, 1,042,599, 1,053,935. Microcapsules which contain the colour formers of formula (1) are suitable for each of these systems as well as for other pressure-sensitive systems.

The capsules are preferably secured to the carrier by means of a suitable adhesive. Since paper is the preferred carrier material, these adhesives are principally paper coating agents, for example gum arabic, polyvinyl alcohol, hydroxymethylcellulose, casein, methyl cellulose or dextrin.

The term "paper" used herein comprises not only normal paper made from cellulose fibres, but also paper in which the cellulose fibres are replaced (partially or completely) by synthetic polymer fibres.

The chromeno compounds of formulae (1) to (3) can also be used as colour formers in a thermoreactive recording material. This recording material contains normally at least one carrier, one colour former, one solid electron acceptor and optionally also one binder. Thermoreactive recording systems comprise for example heat sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks.

The thermoreactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor at those points where heat is applied and the desired colour develops at once.

Suitable developers are the same electron acceptors as are used in pressure-sensitive papers. Examples of developers are the clays and phenolic resins already mentioned, or phenolic compounds, for example 4-tert-butylphenol, 4-phenylphenol, 4-hydroxydiphenyl oxide, α-naphthol, β-naphthol, 4-hydroxymethyl benzoate, 4-hydroxyacetophenone, 2,2'-dihydroxydiphenyl, 4,4'-isopropylidene-diphenyl, 4,4'-isopropylidene-bis-(2-methylphenol), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and aliphatic dicarboxylic acids, for example tartaric acid, oxalic acid, maleic acid, citric acid, citraconic acid or succinic acid.

Fusible, film-forming binders are preferably used for the production of the thermoreactive recording material. These binders are normally water-soluble, whereas the colour formers and the developer are insoluble in water. The binder should be able to disperse and fix the colour former and the developer at room temperature. By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further ingredients. To improve the degree of whiteness, to facilitate the printing of papers, and to prevent the heated pen from sticking, the coatings can contain, for example, talc, $TiO_2$, $ZnO$ or $CaCO_3$ or also organic pigments, for example urea/formaldehyde polymers. In order to effect the colour formation only within a limited temperature range, it is possible to add substances such as urea, thiourea, acetanilide, phthalic anhydride or other appropriate fusible products which induce the simultaneous melting of the colour former and developer.

In the following Manufacturing Directions and Examples, the percentages are by weight unless otherwise indicated.

Manufacturing Directions

A. A solution of 11.6 g of 7-diethylamino-4-methyl-coumarin in 70 ml of tetrahydrofurane is added dropwise to a Grignard solution of 2.5 g of magnesium and 20 g of 4-dimethylamino-1-bromobenzene in 150 ml of tetrahydrofurane. The mixture is then stirred for 18 hours at boiling temperature. Then a 1 N hydrochloric acid solution is added and the reaction mixture is heated to the boil. With cooling, the reaction mixture is made alkaline with a 2 N sodium hydroxide solution and extracted with chloroform. The chloroform phases are dried over magnesium sulphate and evaporated to dryness. The residue is dissolved in cyclohexane and the solution is heated to the boil, then cooled, and, after the addition of silica gel, filtered. The filtrate is concentrated and the residual oil is triturated with a small amount of petroleum ether, whereupon it crystallises, affording 5.2 g of a compound of the formula

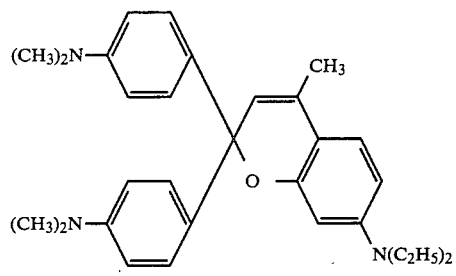

(11)

which melts at 112°–114° C.

B. The procedure described in Manufacturing Direction A is repeated, replacing the 7-diethylamino-4-methyl-coumarin by equimolar amounts of coumarin or 5,6-benzocoumarin, to give the colour formers of the formulae (12) and (13) listed in the table.

C. 2.7 g of 1,1-bis-(4′-dimethylaminophenyl)-propene and 1.7 g of 5-nitrosalicylaldehyde are dissolved in 30 ml of ethanol. The solution is then refluxed for 18 hours with the addition of 4 drops of glacial acetic acid. When the reaction is complete, 50 ml of a 1 N sodium hydroxide solution are added to the mixture, which is then extracted with ether. After removal of the ether, the residue is recrystallised from ethanol, to give the colour former of the formula (14) listed in the table.

D. The procedure of Manufacturing Direction C is repeated, replacing the 5-nitrosalicylaldehyde by an equimolar amount of 3-bromo-5-nitrosalicyl aldehyde, to give the colour former of the formula (15) listed in the table.

TABLE

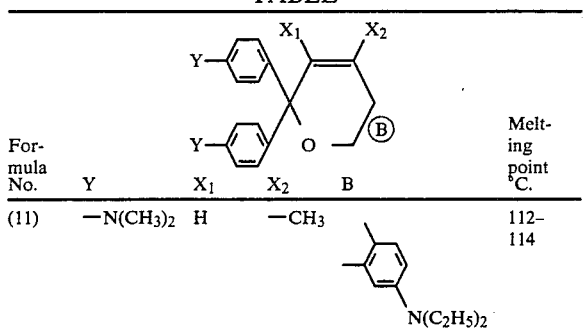

| Formula No. | Y | $X_1$ | $X_2$ | B | Melting point °C. |
|---|---|---|---|---|---|
| (11) | —N(CH$_3$)$_2$ | H | —CH$_3$ | (4-N(C$_2$H$_5$)$_2$-phenyl) | 112–114 |
| (12) | —N(CH$_3$)$_2$ | H | H | (phenyl) | 154–155 |
| (13) | —N(CH$_3$)$_2$ | H | H | (naphthyl) | 220–221 |
| (14) | —N(CH$_3$)$_2$ | —CH$_3$ | H | (4-NO$_2$-phenyl) | 170–171 |
| (15) | —N(CH$_3$)$_2$ | —CH$_3$ | H | (3-Br-5-NO$_2$-phenyl) | 176–177 |

EXAMPLE 1

Production of a pressure-sensitive copying paper

A solution of 3 g of the chromeno compound of formula (11) in 97 g of partially hydrogenated terphenyl is emulsified in a solution of 12 g of pigskin gelatin in 88 g of water of 50° C. A solution of 12 g of gum arabic in 88 g of 50° C. is then added, followed by the addition of 200 ml of water of 50° C. The resultant emulsion is poured into 600 g of ice water, whereupon the coacervation is effected. A sheet of paper is coated with the resultant suspension of microcapsules and dried. A second sheet of paper is coated with silton clay. The first sheet and the sheet of paper coated with silton clay are laid on top of each other with the coated sides face to face.

Pressure is exerted by writing by hand or typewriter and a blue copy of excellent lightfastness develops on the sheet which is coated with clay.

EXAMPLE 2

Production of a thermoreactive paper 6 g of an aqueous dispersion which contains 1.57% of the chromeno compound of formula (13) and 6.7% of polyvinyl alcohol are mixed with 134 g of an aqueous dispersion which contains 14% of 4,4-isopropylidenediphenol, 8% of attapulgite clay and 6% of polyvinyl alcohol. This mixture is applied to a paper and dried. Contacting the paper with a heated ball-point pen produces a vivid bluish-green colour of excellent lightfastness.

What is claimed is:

1. A pressure- or heat-sensitive recording material comprising a support containing or coated with at least one color-forming agent which is a 2,2-diarylchromeno compound of the formula

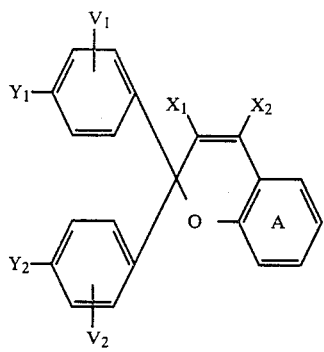

wherein $V_1$ and $V_2$ each represent hydrogen, chlorine, lower alkyl or lower alkoxy, $Y_1$ and $Y_2$ each represent hydrogen, —O—$R_1$ or

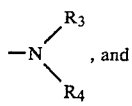

$X_1$ and $X_2$, each independently of the other, represent hydrogen, alkyl of up to 12 carbon atoms which is unsubstituted or represent benzyl, phenyl, or benzyl or phenyl which is substituted by chlorine, nitro, lower alkyl, lower alkoxy or the amino group

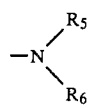

the ring A is unsubstituted or substituted by halogen, nitro, lower alkyl, —O—$R_5$ or

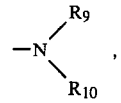

or contains a fused benzene ring, and $R_1$, $R_2$, $R_3$, $R_4$ $R_5$ and $R_6$, each independently of the other, represent alkyl of not more than 12 carbon atoms which is unsubstituted or substituted by cyano or lower alkoxy, or represents cycloalkyl, phenyl, benzyl, or phenyl or benzyl which is substituted by chlorine, nitro, lower alkyl or lower alkoxy, or each of the pairs of substituents $R_1$ and $R_2$, $R_3$ and $R_4$, $R_5$ and $R_6$, together with the nitrogen atom to which said pair is attached, forms a 5- or 6- membered heterocyclic radical.

2. A recording material as claimed in claim 1, wherein $Y_1$ and $Y_2$, represent hydrogen, —O—$R_7$ or

$X_1$ represents hydrogen, lower alkyl, benzyl, phenyl, or benzyl which is substituted by chlorine, $X_2$ represents hydrogen, lower alkyl, benzyl, phenyl, benzyl which is substituted by chlorine or lower alkyl, or phenyl which is substituted by chlorine, nitro, lower alkyl, lower alkoxy or by the amino group

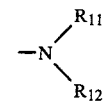

and the ring A is unsubstituted or substituted by halogen, nitro, lower alkyl, —O—$R_{11}$ or

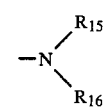

or contains a fused benzene ring, whilst $R_7$, $R_8$, $R_9$, $R_{10}$, $R_{11}$ and $R_{12}$, each independently of the other, represent alkyl of 1 to 12 carbon atoms, cycloalkyl, phenyl, benzyl or phenyl or benzyl which is substituted by chlorine, lower alkyl or lower alkoxy, or each of the pair of substituents $R_7$ and $R_8$, $R_9$ and $R_{10}$, $R_{11}$ and $R_{12}$, together with the nitrogen atom to which said pair is attached, represents a 5- or 6-membered heterocyclic ring.

3. A recording material as claimed in claim 2, wherein $V_1$ and $V_2$, each represent hydrogen, chlorine, methyl, methoxy or ethoxy, $Y_1$ and $Y_2$, each represent hydrogen, lower alkoxy, phenoxy, benzyloxy or $$-N\begin{matrix}R_{13}\\R_{14}\end{matrix},$$

$X_1$ represents hydrogen or lower alkyl, and $X_2$ represents hydrogen, lower alkyl, benzyl or phenyl, and the ring A is unsubstituted or substituted by halogen, nitro, or $$-N\begin{matrix}R_{15}\\R_{16}\end{matrix}$$

or contains a fused benzene ring, whilst $R_{13}$, $R_{14}$, $R_{15}$ and $R_{16}$, each independently of the other, represent lower alkyl, phenyl or benzyl.

4. A recording material as claimed in claim 3 wherein the colour former has the formula

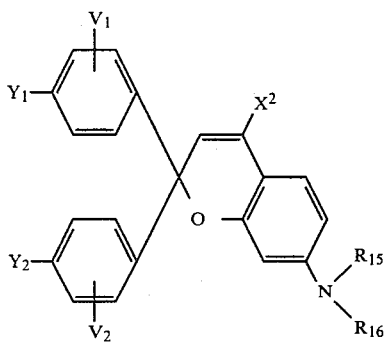

wherein $V_1$, $V_2$, $Y_1$, $Y_2$, $R_{15}$ and $R_{16}$ are as defined in claim 3 and $X_2$ represents hydrogen, lower alkyl, benzyl or phenyl.

5. A recording material as claimed in claim 2 wherein the colour former has the formula

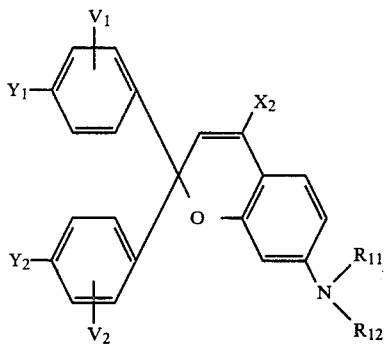

wherein $V_1$, $V_2$, $Y_1$, $Y_2$, $R_{11}$ and $R_{12}$ are as defined in claim 2 and $X_2$ represents hydrogen, lower alkyl, benzyl, phenyl, or benzyl which is substituted by chlorine.

6. A recording material as claimed in claim 1, wherein $Y_1$ and $Y_2$ represent an amino group

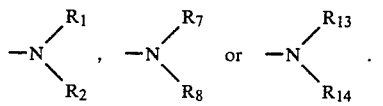

7. A recording material as claimed in claim 6, wherein the ring A is substituted by a di-lower alkylamino group.

8. A recording material as claimed in claim 1 wherein the colour former has the formula

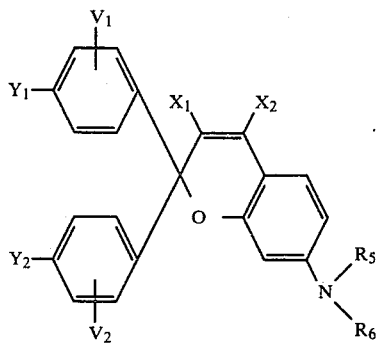

wherein each of $X_1$ and $X_2$ represents hydrogen, alkyl of up to 12 carbon atoms which is unsubstituted or represents benzyl or phenyl which is unsubstituted or substituted by chlorine, nitro, lower alkyl, lower alkoxy or

and $V_1$, $V_2$, $Y_1$, $Y_2$, $R_3$, $R_4$, $R_5$ and $R_6$ are as defined in claim 1.

9. A recording material as claimed in claim 1 wherein the colour former has the formula

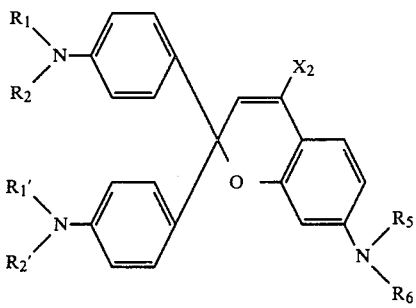

wherein each of $R_1$, $R_2$, $R_1'$, $R_2'$, $R_5$, $R_6$ and $X_2$ represents alkyl of 1 to 4 carbon atoms.

10. A recording material as claimed in claim 1 wherein at least one of the substituents $Y_1$ and $Y_2$ or of the substituents in the ring A represents

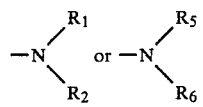

in the 2,2-diarylchromeno compound.

11. A recording material as claimed in claim 1 which is pressure-sensitive.

12. A pressure-sensitive recording material as claimed in claim 11, which contains the 2,2-diarylchromeno compound dissolved in an organic solvent, and at least one electron acceptor.

13. A pressure-sensitive recording material as claimed in claim 12, wherein the solution of the colour former in an organic solvent is contained in microcapsules which can be ruptured by pressure.

14. A pressure-sensitive recording material as claimed in claim 13, wherein the encapsulated colour former is applied in the form of a layer to the reverse side of a transfer sheet and the electron acceptor is applied in the form of a layer to the face of the receiving sheet, the sheets being arranged such that in use the coated sides contact each other.

15. A pressure-sensitive recording material as claimed in claim 12 wherein the electron acceptor is attapulgite clay, silton clay, or a phenolformaldehyde resin.

16. A pressure-sensitive recording material as claimed in claim 1, which contains at least one other colour former together with the 2,2-diarylchromeno compound.

17. A heat-sensitive recording material as claimed in claim 1, which contains in at least one layer at least one colour former, at least one electron acceptor and, optionally, at least one binder, wherein the colour former is as defined in claim 1.

18. A heat-sensitive recording material as claimed in claim 17, wherein the electron acceptor is attapulgite clay, silton clay, a phenolic compound, a phenolic resin or a solid organic acid.

19. A heat-sensitive composition which contains at least one colour former as defined in claim 1, at least one electron acceptor and, optionally, at least one binder.

* * * * *